United States Patent [19]

Tiers

[11] Patent Number: 4,818,899
[45] Date of Patent: Apr. 4, 1989

[54] SECOND HARMONIC GENERATION BY CARBAMIC ACID DERIVATIVES

[75] Inventor: George V. D. Tiers, St. Paul, Minn.

[73] Assignee: Minnesota Mining and Manufacturing Company, St. Paul, Minn.

[21] Appl. No.: 937,234

[22] Filed: Dec. 3, 1986

[51] Int. Cl.$^4$ ............................ G02F 1/03; H03F 7/00
[52] U.S. Cl. ....................................... 307/425; 372/22; 350/311; 252/600; 252/582
[58] Field of Search ............... 372/21, 22; 307/425, 307/427; 350/96.34, 311, 353, 362; 252/582, 600

[56] References Cited

U.S. PATENT DOCUMENTS

| | | | |
|---|---|---|---|
| 3,395,329 | 7/1968 | Rentzepis | 321/69 |
| 3,431,484 | 3/1968 | Pao et al. | 321/69 |
| 3,858,124 | 12/1974 | Bass et al. | 332/7.51 |
| 4,199,698 | 4/1980 | Bethea et al. | 307/425 |
| 4,208,501 | 6/1980 | Yee et al. | 526/259 |
| 4,376,899 | 3/1983 | Chemla et al. | 307/425 |
| 4,431,263 | 2/1984 | Garito | 350/96.34 |
| 4,579,915 | 4/1986 | Choe | 525/435 |
| 4,624,872 | 11/1986 | Stuetz | 252/299.01 X |

FOREIGN PATENT DOCUMENTS

| | | |
|---|---|---|
| 0207358 | 7/1987 | European Pat. Off. . |
| 0235955 | 9/1987 | European Pat. Off. . |
| 3236626 | 5/1984 | Fed. Rep. of Germany . |
| 2113684 | 10/1983 | United Kingdom . |

OTHER PUBLICATIONS

Twieg and Jair, "Organic Materials for Optical Second Harmonic Generation", Chapter 3 of "Nonlinear Optical Properties . . ." Williams, Editor, ACS publisher 1983.

Badan et al. "Nonlinear Organic Crystals . . . " Chapter 4 of Nonlinear Optical Properties . . . William Editor, ACS publication 1985.

Kurtz et al, J Appl. Phys. 39, 3798 (1968).

*Nonlinear Optical Properties of Organic Molecules and Crystals*, vol. 2, edited by D. S. Chemla and J. Zyss, Academic Press, Inc., Harcourt Brace Jovanovich, Publishers (1987), Appendix I, p. 233.

The Contribution of $\pi$ Electrons to Second Harmonic Generation in Organic Molecules, C. W. Dirk, R. J. Twieg, and G. Wagniere, J. Am. Chem. Soc. 1986, 108, 5387–5395.

Chemical Abstracts, vol. 106, 1987: Organic Materials for Second Harmonic Generation, Twieg, R. J., International Business Machines Corp., San Jose, California, Report 1985, 106:57923q.

Journal of the Optical Society of America B, vol. 4, No. 6, Jun. 1987, pp. 977–986 and pp. 998–1012.

*Primary Examiner*—Matthew A. Thexton
*Assistant Examiner*—Catherine S. Kilby
*Attorney, Agent, or Firm*—Donald M. Sell; Walter N. Kirn; David L. Weinstein

[57] ABSTRACT

Devices for and method of generating coherent second harmonic light radiation. The devices comprise a laser source of coherent light radiation at a fixed fundamental frequency, a crystalline N-aryl carbamyl compound that crystallizes in a non-centrosymmetric configuration, means for directing the output radiation of the laser onto the crystalline chiral N-aryl carbamyl compound, and output means for utilizing the second harmonic frequency.

14 Claims, 1 Drawing Sheet

SECOND HARMONIC GENERATION BY CARBAMIC ACID DERIVATIVES

TECHNICAL FIELD

This invention is concerned with materials for nonlinear optical devices for the conversion of optical energy at one frequency to optical energy at another frequency.

BACKGROUND OF THE INVENTION

Laser techniques have been developed that make it convenient to obtain various fundamental frequencies of coherent laser light by utilizing solid, gas, and liquid media. Outstanding among these are solid-state lasers, because they are small, inexpensive, and require no maintenance; however their output is limited to the near-infrared region of the spectrum and is of low power. However, in many applications, laser light having frequencies above those conveniently obtainable is required. Nonlinear optical crystals have, therefore, frequently been employed to convert coherent laser light of a fundamental frequency into laser light of the second harmonic, that is to say, laser light with a frequency twice the fundamental frequency. This conversion is termed "second-harmonic-generation" (SHG).

In the prior art, monocrystalline forms of potassium dihydrogen phosphate (KDP), ammonium dihydrogen phosphate (ADP), barium sodium niobate ($BaNaNbO_3$), and lithium niobate ($LiNbO_3$) have been used for generating higher frequency harmonics. Monocrystalline KDP and ADP, while offering greater resistance to optical-irradiation-induced surface damage due to laser beam bombardment, do not exhibit large optical nonlinearities. This rendered these crystals unsuitable for higher harmonic frequency generation by conversion of light derived from low-power sources. In contrast, $BaNaNbO_3$ and $LiNbO_3$ show larger nonlinearities but, unfortunately, a low resistance to optical damage. In this regard, the term "resistance to optical damage" means the number of times (shots) the surface of a crystalline material can suffer bursts of laser radiation of a given power density in watts per unit area before the subject crystal shows signs of opacity. Thus, a crystal showing high resistance can sustain a larger number of shots than a crystal of low resistance for the same power density of the incident laser beams. These niobate materials are also mechanically and thermally fragile, and are marginal in SHG efficiency at power levels that are characteristic of laser diodes.

The possibility of using organic molecules in nonlinear optical devices has generated much interest recently because a large number of molecules are available for investigation. Some substituted aromatic molecules are known to exhibit large optical nonlinearities. The possibility of such an aromatic molecule having large optical nonlinearities is enhanced if the molecule has donor and acceptor groups bonded at opposite ends of the conjugated system of the molecule. The potential utility for very high frequency application of organic materials having large second-order and third-order nonlinearities is greater than that for conventional inorganic electro-optic materials because of the bandwidth limitations of inorganic materials. Furthermore, the properties of organic materials can be varied to optimize mechanical and thermo-oxidative stability and laser damage threshold.

U.S. Pat. No. 4,199,698 discloses that the nonlinear optical properties of 2-methyl-4-nitroaniline (MNA) make it a highly useful material in nonlinear devices that convert coherent optical radiation including a first frequency into coherent optical radiation including a second, typically higher, frequency. The nonlinear devices have means for introducing coherent radiation of a first frequency into the MNA and means for utilizing coherent radiation emitted from the MNA at a second frequency.

U.S. Pat. No. 4,431,263 discloses that diacetylenes and polymers formed from diacetylenic species, which are amenable to close geometric, steric, structural, and electronic control, provide nonlinear optic, waveguide, piezoelectric, and pyroelectric materials and devices. Diacetylenes which are crystallizable into crystals having a noncentrosymmetric unit cell may form single crystals or, if they do not, may possibly be elaborated into a polar thin film upon a substrate by the Langmuir-Blodgett technique. Such films often may be polymerized either thermally or by irradiation for use in nonlinear optical systems. Diacetylenes are covalently bonded to substrates through the employment of silane species and subsequently polymerized to yield nonlinear optic devices asserted to have high structural integrity in addition to high efficiencies and optical effects.

Other U.S. patents relating to non-linear optical properties of organic materials include U.S. Pat. Nos. 4,208,501; 4,376,899; and 4,579,915.

SUMMARY OF THE INVENTION

The present invention provides a laser generator of coherent second harmonic light radiation by utilizing certain chiral carbamic acid derivatives and a method of generating coherent second harmonic light radiation with such a device.

In general, second harmonic generators of this invention comprise, in combination, a laser source of coherent light radiation at a fixed fundamental frequency, an organic molecular crystalline compound selected from particular classes of chiral carbamic acid derivatives, e.g. chiral N-aryl carbamyl compounds, means for directing the output radiation of the laser onto the organic molecular crystalline carbamic acid derivatives, and output means for utilizing the second harmonic frequency.

In another aspect, all of the chiral carbamic acid derivatives described herein are novel.

DETAILED DESCRIPTION

The carbamic acid derivatives of this invention are characterized as N-aryl carbamyl compounds which are chiral, crystalline, and non-centrosymmetric. As used herein, the term "chiral" means that the molecule and its mirror image are not superposable. N-Aryl carbamyl compounds that have been found to exhibit second harmonic generation are crystalline in form. N-Aryl carbamyl compounds suitable for this invention are non-centrosymmetric species which have no center of symmetry on either the molecular or crystalline unit cell level.

Chiral N-aryl carbamyl compounds that have been found to be useful for this invention can be represented by the following general formula $$R^1R^2NCOR^5 \quad (I)$$

which may be conveniently categorized into two major subclasses, namely the ureas (II) and the urethanes (III):

$$R^1R^2NCONR^3R^4 \quad (II)$$

$$R^1R^2NCO_2R^3 \quad (III)$$

where
$R^1$ represents an aryl group having no more than eighteen carbon atoms,
$R^2$ represents hydrogen or an alkyl group, preferably having one to six carbon atoms,
$R^3$ represents a carbon-containing chiral group,
$R^4$ represents hydrogen, an alkyl group, preferably having one to six carbon atoms, a chiral group, or $R^3$ and $R^4$ together, along with the nitrogen atom to which they are attached, form a catenated heterocyclic ring containing from 3 to 7 ring members, and
$R^5$ represents $-NR^3R^4$ or $-OR^3$.

$R^1$ may be substituted or unsubstituted. If $R^1$ is substituted, the substituents are preferably selected from the group consisting of nitro, alkoxy, acyloxy, acyl, alkoxycarbonyl, aryloxy, alkaryloxy, aralkoxy, alkylthio, arylthio, alkyl, haloalkyl, aryl, aralkyl, alkaryl, cyano, and halo. The preferred substituents are nitro, acyl, alkoxycarbonyl, and cyano, the most preferred substituent being the nitro group.

If $R^2$ is an alkyl group, it may be substituted or unsubstituted. The $R^2$ alkyl group may be substituted with any substituent that does not adversely affect the second harmonic generating properties of the urea or urethane molecule of this invention.

The chiral groups $R^3$ and $R^4$ can be derived from chiral amines and alcohols, which will be described hereinafter.

If $R^3$, $R^4$, and the nitrogen to which they are attached form a ring, the carbon atoms in the ring may be interrupted by atoms selected from nitrogen, oxygen, or sulfur.

Although the molecule $R^1R^2NCOR^5$ must be chiral, the sign of its optical activity is not critical, i.e. it does not matter whether the molecule rotates the plane of vibration of polarized light to the right or to the left.

Representative examples of N-aryl carbamyl compounds suitable for use in this invention include those where $R^2$ and $R^4$ represent hydrogen, $R^3$ represents (R)- or (S)-alpha-methylbenzyl or (R)- or (S)-1-(alpha-naphthyl)ethyl and $R^1$ represents a group selected from the group consisting of 2-nitrophenyl, 3-nitrophenyl, 4-nitrophenyl, 4-cyanophenyl, 2,4-dinitrophenyl, 2-fluoro-5-nitrophenyl, 2-cyano-4-nitrophenyl, 2,6-dichloro-4-nitrophenyl, 2-benzoyl-4-nitrophenyl, 4'-nitrobiphenyl-4-yl, 4-(2-(4-nitrophenyl)ethenyl)phenyl, 4-nitro-1-naphthyl, 5-nitro-1-naphthyl, 1-nitro-2-naphthyl, 6-nitro-2-naphthyl, 8-nitro-2-naphthyl, 7-nitro-2-phenanthryl, and 7-nitro-2-fluorenyl. Additional representative examples of N-aryl carbamyl compounds suitable for use in this invention include those where $R^2$ and $R^4$ represent hydrogen, $R^3$ represents (R)- or (S)-1-hydroxy-2-propyl and $R^1$ represents a group selected from the group consisting of 2-nitrophenyl, 3-nitrophenyl, 4-nitrophenyl, 2-chloro-4-nitrophenyl, 2-methyl-4-nitrophenyl, 2-methoxy-4-nitrophenyl, 4'-nitrobiphenyl-4-yl, 4-(2-(4-nitrophenyl)ethenyl)phenyl, 4-nitro-1-naphthyl, 5-nitro-1-naphthyl, and 8-nitro-2-naphthyl.

Still additional representative examples of N-aryl carbamyl compounds suitable for use in this invention include those where $R^2$ represents hydrogen, $R^5$ represents XY where X represents $-NR^4$ or $-O-$ and Y represents (R)- or (S)-1-(ethoxycarbonyl)ethyl, and $R^1$ represents 2-nitrophenyl, 3-nitrophenyl, 4-nitrophenyl, 4-cyanophenyl, 2-chloro-4-nitrophenyl, 2-methyl-4-nitrophenyl, 2-methoxy-4-nitrophenyl, 4'-nitrobiphenyl-4-yl, 4-(2-(4-nitrophenyl)ethenyl)phenyl, 4-nitro-1-naphthyl, 5-nitro-1-naphthyl, and 8-nitro-2-naphthyl respectively.

Species of N-aryl carbamyl compounds that are suitable for use in this invention include the following:
N-(5-nitronaphth-1-yl)-N'-(R/S)alpha-methylbenzylurea,
N-(1-nitronaphth-2-yl)-N'-(R/S)alpha-methylbenzylurea,
N-(6-nitronaphth-2-yl)-N'-(R/S)alpha-methylbenzylurea,
N-(8-nitronaphth-2-yl)-N'-(R/S)alpha-methylbenzylurea,
N-(4'-nitrobiphenyl-4-yl)-N'-(R/S)alpha-methylbenzylurea,
N-(7-nitrofluoren-2-yl)-N'-(R/S)alpha-methylbenzylurea,
N-(7-nitrophenanthren-2-yl)-N'-(R/S)alpha-methylbenzylurea,
N-(7-nitro-9,10-dihydrophenanthren-2-yl)-N'-(R/S)alpha-methylbenzylurea,
N-(4'-nitrostilben-2-yl)-N'-(R/S)alpha-methylbenzylurea,
N-(6-nitrodibenzofuran-3-yl)-N'-(R/S)alpha-methylbenzylurea,
N-ethyl-N-(4-nitrophenyl)-N'-(R/S)alpha-methylbenzylurea,
N-(5-nitronaphth-1-yl)-N'-(R/S)-1-(alpha-naphthyl)ethylurea,
N-(1-nitronaphth-2-yl)-N'-(R/S)-1-(alpha-naphthyl)ethylurea,
N-(6-nitronaphth-2-yl)-N'-(R/S)-1-(alpha-naphthyl)ethylurea,
N-(8-nitronaphth-2-yl)-N'-(R/S)-1-(alpha-naphthyl)ethylurea,
N-(4'-nitrobiphenyl-4-yl)-N'-(R/S)-1-(alpha-naphthyl)ethylurea,
N-(7-nitrofluoren-2-yl)-N'-(R/S)-1-(alpha-naphthyl)ethylurea,
N-(7-nitrophenanthren-2-yl)-N'-(R/S)-1-(alpha-naphthyl)ethylurea,
N-(7-nitro-9,10-dihydrophenanthren-2-yl)-N'-(R/S)-1-(alpha-naphthyl)ethylurea,
N-(4'-nitrostilben-2-yl)-N'-(R/S)-1-(alpha-naphthyl)ethylurea,
N-(6-nitrodibenzofuran-3-yl)-N'-(R/S)-1-(alpha-naphthyl)ethylurea,
N-ethyl-N-(4-nitrophenyl)-N'-(R/S)-1-(alpha-naphthyl)ethylurea,
N-(5-nitronaphth-1-yl)-(D/L)-1-(methoxycarbonyl)ethylurethane,
N-(1-nitronaphth-2-yl)-(D/L)-1-(methoxycarbonyl)ethylurethane,
N-(6-nitronaphth-2-yl)-(D/L)-1-(methoxycarbonyl)ethylurethane,
N-(8-nitronaphth-2-yl)-(D/L)-1-(methoxycarbonyl)ethylurethane, N-(4'-nitrobiphenyl-4-yl)-(D/L)-1-(methoxycarbonyl)ethylurethane,
N-(7-nitrofluoren-2-yl)-(D/L)-1-(methoxycarbonyl)ethylurethane,
N-(7-nitrophenanthren-2-yl)-(D/L)-1-(methoxycarbonyl)ethylurethane,
N-(7-nitro-9,10-dihydrophenanthren-2-yl)-(D/L)-1-(methoxycarbonyl)ethylurethane,
N-(4'-nitrostilben-2-yl)-(D/L)-1-(methoxycarbonyl)ethylurethane,
N-(6-nitrodibenzofuran-3-yl)-(D/L)-1-(methoxycarbonyl)ethylurethane,
N-ethyl-N-(4-nitrophenyl)-(D/L)-1-(methoxycarbonyl)ethylurethane,
N-(5-nitronaphth-1-yl)-(D/L)-1-(ethoxycarbonyl)ethylurethane,
N-(1-nitronaphth-2-yl)-(D/L)-1-(ethoxycarbonyl)ethylurethane,
N-(6-nitronaphth-2-yl)-(D/L)-1-(ethoxycarbonyl)ethylurethane,
N-(8-nitronaphth-2-yl)-(D/L)-1-(ethoxycarbonyl)ethylurethane,
N-(4'-nitrobiphenyl-4-yl)-(D/L)-1-(ethoxycarbonyl)ethylurethane,
N-(7-nitrofluoren-2-yl)-(D/L)-1-(ethoxycarbonyl)ethylurethane,
N-(7-nitrophenanthren-2-yl)-(D/L)-1-(ethoxycarbonyl)ethylurethane,
N-(7-nitro-9,10-dihydrophenanthren-2-yl)-(D/L)-1-(ethoxycarbonyl)ethylurethane,
N-(4'-nitrostilben-2-yl)-(D/L)-1-(ethoxycarbonyl)ethylurethane,
N-(6-nitrodibenzofuran-3-yl)-(D/L)-1-(ethoxycarbonyl)ethylurethane,
N-ethyl-N-(4-nitrophenyl)-(D/L)-1-(ethoxycarbonyl)ethylurethane, In the foregoing compounds, the term (R/S) means either (R) or (S) enantiomer, but does not mean a mixture of (R) and (S) enantiomers; the term (D/L) means either (D) or (L) enantiomer, but does not mean a mixture of (D) and (L) enantiomers.

Compounds of this invention can be conveniently prepared by well-known methods, such as by the reaction of a suitable aryl isocyanate with the appropriate chiral amine or alcohol to provide the resultant urea or urethane, respectively.

Chiral amines or alcohols that are preferred for the preparation of the ureas and urethanes of this invention are those compounds wherein the chiral group $R^5$ has a molecular weight range from about 50 to about 300 with a preferable range from about 70 to about that of the weight of $R^1$. It is more preferred that the chiral group have a molecular weight ranging from about 70% to 90% of that of the weight of $R^1$. Chiral groups having molecular weights above about 300 are generally less useful in the practice of this invention, as they dilute the active part of the molecule. Preferred classes of chiral groups are those for which at least one asymmetric carbon atom is adjacent to the carbon atom attached to the linking group X of $R^5$ (i.e. —$NR^4$ or —O—), and the most preferred class is that for which the carbon atom attached to the linking group X of $R^5$ is itself asymmetric.

The urea and urethane compounds of this invention are substantially transparent to electromagnetic radiation having wavelengths from about 0.5 to about 1.5 micrometers. Accordingly, they are useful in second harmonic generators wherein both incident radiation and emergent radiation range from about 0.5 micrometer to about 1.5 micrometers; many of the carbamyl compounds are useful to as low as about 0.4 micrometer, or even somewhat lower.

Generally, the urethanes are preferred in the situation where the SHG signal is to be near 0.4 micrometer, and especially if the signal is lower than that wavelength, because, other factors being equal, their region of transparency extends slightly further into the ultraviolet region than does that of the ureas. Conversely, the ureas are preferred in other situations because their melting points are generally higher than those of urethanes, which will permit them to be used under somewhat more severe conditions of temperature and, thus, of laser power level.

Devices that are capable of generating coherent second harmonic light radiation with the chiral N-aryl carbamyl compounds described herein are well known in the art. Representative examples of such devices are described in U.S. Pat. Nos. 3,395,329, 3,431,484, and 3,858,124, all of which are incorporated herein by reference for the purpose of describing devices which can incorporate the chiral N-aryl carbamyl compounds described herein and exhibit efficient second harmonic generation by means of such incorporation.

Crystals of the chiral N-aryl carbamyl compounds exemplified herein were evaluated for SHG efficiency using the second harmonic generation (SHG) powder test described in Kurtz et al., J. Appl. Phys. 39, 3798 (1968). Each sample was crushed (not ground) and sieved. This step was often time-consuming due to the property of piezoelectricity (shown by all non-centrosymmetric crystals) which acts to cause crystals to cling together and not pass through the sieve; often it was necessary to repeatedly anneal the crushed crystals during the sieving operation. The sample was then mixed with a fluid, i.e., a liquid, to minimize scattering, refraction, or phase-incoherence caused by differences in the index of refraction between the particles and the ambient atmosphere. The index-matched sample was placed between cell flats spaced 0.35±0.02 mm apart. Particles having mean diameters such as to pass through a 180 micrometer screen but be retained by a 75 micrometer screen were used. Each sample was mixed with a drop of index matching fluid (Cargille Scientific Co. n=1.63 or n=1.58 fluids or n=1.631 polyphenylether described in U.S. Pat. No. 3,034,700). The samples were not index-matched critically, so that the actual SHG efficiencies may be markedly higher than those reported in the examples.

Figure 1:
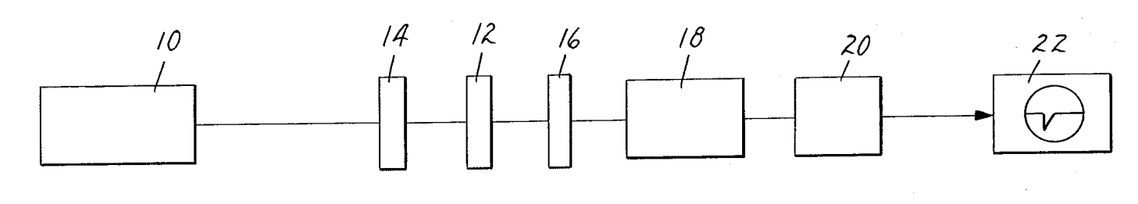
The drawing is a diagrammatic representaton of a suitable arrangement for demonstrating the second harmonic generating properties of the carbamic acid derivatives of this invention.

Referring now to FIG. 1, infrared radiation at 1064 nm from a Q-switched Nd-YAG laser 10 was weakly focused onto the cell 12 containing the prepared sample. In the device illustrated in FIG. 1, the means, e.g. a lens, for directing the output radiation of the laser first through a filter 14 (Corning CS2-60 color filter used to block any radiation at 532 nm) and then onto the cell 12 containing the carbamyl compound sample was integrated into the laser 10 and is not shown as a separate component. Such means for directing the filtered output radiation of the laser onto the organic molecular crystalline compound sample are well-known to one of ordinary skill in the art. An infrared blocking filter 16 placed behind the sample allowed only the second harmonic frequency radiation to pass through a ¼ meter monochromator 18 tuned at 532 nm. The output of the monochromator 18 was directed to a photomultiplier tube 20, and the resulting signal was processed by a boxcar averager 22 that averages over many laser pulses. Urea was the chosen standard because of its moderately high second order coefficient and its ready availability. It is important to recrystallize the urea to form transparent crystals of a size greater than about 200 micrometers in their smallest dimension, so that the crushed particles made from them will be single crystals. The urea standard was prepared in the same manner as the samples. The urea standard was index-matched reasonably well, with a mismatch of about 0.01. The reported efficiency of a sample is its SHG signal normalized to that of the urea standard measured under the same experimental conditions.

Compounds prepared according to the following examples are summarized in Tables I-XIII and were examined to determine their melting points (m.p.), their sixteen strongest X-ray signals for lattice spacings (d-spacings) derived from diffraction angles, together with their relative intensities, and their SHG efficiency relative to urea. The sieved SHG samples were X-ray analyzed to establish their powder diffraction patterns, in the exact crystalline state on which the SHG tests were made. Unlike the melting point elemental analysis, NMR, or mass spectra, these diffraction patterns are highly characteristic not only for a particular compound but also for its particular crystal form. It should be understood that relative line intensities may vary systematically due to varying degrees of sample orientation on the flat plastic slide which carries the sample into the Automatic Powder Diffractometer, Model No. APD 3600, Philips Electronics Instruments, Inc., Mahwah, N.J.; however, the d-spacing will remain essentially unaffected. The solvent or solvent mixtures used for crystallization of the particular compound are also indicated. The particular materials and the amounts thereof recited in these examples, as well as other conditions and details, should not be construed to unduly limit this invention.

EXAMPLE 1

N-(4-nitrophenyl)-N'-(R-alpha-methyl-benzyl)urea (m.p. 179.5°–180.5° C.) was prepared by reacting freshly-purified commercial 4-nitrophenyl isocyanate with commercial R(+)-alpha-methyl-benzylamine in dried chlorobenzene.

Spectroscopic grade chlorobenzene (180 ml) was freshly boiled to remove water, and 40 ml of it was kept warm in a 50 ml Erlenmeyer flask. In a second 50 ml Erlenmeyer flask was placed 8.21 g (0.050 mole) of fresh commercial 4-nitrophenyl isocyanate (Eastman Chemical Co.). Because its hydrolysis product present as an impurity, bis-(4-nitrophenyl)urea, was virtually insoluble in chlorobenzene, a milky yellow solution was produced when 40 ml of this solvent was added. To remove the impurity, the isocyanate solution was filtered directly into a 250 ml Erlenmeyer flask containing 100 ml of still-warm chlorobenzene, into which had been placed 6.06 g (0.050 mole) of R(+)-alpha-methyl-benzylamine (0.050 mole), (98+%, Aldrich Chem. Co., Milwaukee, WI).

A funnel equipped with a Whatman #54 9 cm filter paper, folded into a cone, was used for filtration. The paper had been dried, weighed, and freshly dried in an oven just prior to use. The funnel delivered directly into the reaction flask, which had been provided with a magnetic stirrer and had been placed on a hot plate. The unused 40 ml warm chlorobenzene was used to wash all isocyanate residues into the reaction mixture. The filtered and washed insoluble yellow impurity, i.e. the aforementioned hydrolysis product, weighed 0.26 g upon drying and corresponded to a 3% impurity level. The reaction mixture became very warm and later deposited crystals copiously; the reaction mixture was then heated to reflux, at which point all crystals redissolved and no precipitate of bis-(4-nitrophenyl)urea was visible. The magnetic stirrer was withdrawn and the solution allowed to cool to bring about crystallization; the resulting crystals had a melting point (m.p.) of 179.5°–180.5° C. This urea compound, in crystals of nominal size of 100 micrometers, i.e. sieved to between 75 and 180 micrometers, showed a SHG efficiency of about 30 times that of the standard urea powder sample. Upon recrystallization from tetrahydrofuran/heptane solvent mixture, the crystals showed a SHG efficiency of about 37 times that of the standard urea powder sample. When, contrary to the established powder SHG test method, certain larger unsieved plate-like crystals (see Example 1A in Table I) were tested in a similar manner, SHG values from 250 to 290 times that of the urea standard were recorded; however the enhancement was due at least in part to sample orientation effects.

The compound prepared in this example was shown to be useful as a nonlinear optical device by means of the following experiment. A thin crystal having a width of 2 mm and a length of 5 mm was placed in and normal to the beam path of a Nd-YAG laser operating in the infrared mode (wavelength of 1.064 micrometers). The light beam emerging from the crystal was aligned along the axis of the beam path of the incident radiation and was visible green light (wavelength of 0.532 micrometer).

The procedure of Example 1 was further utilized to prepare the ureas set forth and described in Tables I, II, III, and IV. Table I sets forth relative SHG efficiencies of ureas that differ primarily in the aryl substituent. Table II sets forth relative SHG efficiencies of 4-nitrophenyl urea compounds having various chiral groups. Table III sets forth the X-ray powder patterns for the ureas of Tables I and II. Table IV sets forth the crystallization solvents for the ureas of Tables I and II.

TABLE I

| Example | Aryl group in chiral urea[1] | m.p.[2] (°C.) | Relative SHG efficiency[3] | Powder quality[4] | Power (mW)[5] |
|---|---|---|---|---|---|
| 1 | 4-NO$_2$C$_6$H$_4$— | 180 | 37. | F. Good | 12 |
| 1A | 4-NO$_2$C$_6$H$_4$— | — | — | — | — |
| 2 | 3-NO$_2$C$_6$H$_4$— | 178 | 0.1 | Fair | 12 |
| 2A | 3-NO$_2$C$_6$H$_4$— | — | — | — | — |
| 3 | 2-NO$_2$C$_6$H$_4$— | 159 | 2.4 | Good | 11 |
| 4 | 2-Cl—C$_6$H$_4$— | 163 | 0.1 | Good | 11 |
| 5 | 3-Cl—C$_6$H$_4$— | 144 | 0.3 | Good | 10 |
| 6 | 4-Cl—C$_6$H$_4$— | 190 | 0.01 | Good | 11 |
| 7 | 3,4-Cl$_2$C$_6$H$_3$— | 172 | 0.04 | Fair | 10 |
| 8 | 4-C$_6$H$_5$—O—C$_6$H$_4$— | 134 | 0.4 | Good | 12 |

TABLE I-continued

| Example | Aryl group in chiral urea[1] | m.p.[2] (°C.) | Relative SHG efficiency[3] | Powder quality[4] | Power (mW)[5] |
|---|---|---|---|---|---|
| 9 | $4\text{-}CH_3O\text{-}C_6H_4\text{-}$ | 180 | 0.02 | Fair | 11 |
| 10 | $1\text{-}C_{10}H_7\text{-}$ | 226 | 0.001 | V. Poor | 11 |
| 11 | $2\text{-}C_{10}H_7\text{-}$ | 186 | 0.1 | Fair | 11 |
| 12 | $3\text{-}CF_3C_6H_4\text{-}$ | 125 | 0.002 | F. Good | 11 |
| 13 | $2\text{-}Cl\text{-}4\text{-}NO_2C_6H_3\text{-}$ | 169 | 0.3 | F. Good | 12 |
| 14 | $2\text{-}CH_3O\text{-}4\text{-}NO_2C_6H_3\text{-}$ | 184 | 0.006 | F. Good | 12 |
| 15 | $2\text{-}CH_3\text{-}4\text{-}NO_2C_6H_3\text{-}$ | 169d | 0.01 | Good | 10 |
| 16 | $4\text{-}N\equiv C\text{-}C_6H_4\text{-}$ | 192 | 0.5 | Good | 12 |
| 17 | 7-$NO_2$-2-fluorenyl ($7\text{-}NO_2\text{-}2\text{-}C_{11}H_8\text{-}$) | 286d | 0.005 | Fair | 10 |

[1] The aryl group of the chiral urea is represented by $R^3$ of formula II. In Examples 1 through 17, inclusive, the chiral group was derived from R-alpha-methylbenzylamine.
[2] d indicates that the compound melts with decomposition.
[3] The relative SHG efficiency is based on the SHG efficiency of urea, which has been assigned a value of 1.0.
[4] Powder quality refers to the clarity, lack of polycrystallinity, and size distribution of the crystal fragments as judged by microscopic examination. As powder quality improves, the measured SHG efficiency improves. F represents "fairly". V represents "very".
[5] mW represents megawatts.

TABLE II

| Example | Chiral group of 4-nitroaryl urea compound[1] | m.p.[2] (°C.) | Relative SHG efficiency[3] | Powder quality[4] | Power (mW)[5] |
|---|---|---|---|---|---|
| 18 | $-HN-\overset{*}{C}H(CH_3)-CH_2OH$ (derived from L-2 amino-1-propanol; L-alaninol) | 159d | 1.07 | Poor | 8.5 |
| 19 | $-N\underset{CH_2CH_2}{\overset{\overset{CO_2H}{\underset{*}{C}}-H}{\diagup\diagdown}}CH_2$ (derived from L-proline) | 210d | 0.8 | Fair | 8.5 |
| 20 | $-N\overset{CH_3}{\underset{|}{C}}H\overset{*}{C}H(OH)-C_6H_5$ with $CH_3$ (derived from l-ephedrine) | 147d | 0.3 | F. Good | 8.3 |
| 21 | $-HN-\overset{*}{C}H(CH_3)CO_2H$ (derived from L-alanine) | 224d | 0.003 | Poor | 8.5 |
| 22 | $-HN-\overset{*}{C}H(CH_3)-CO_2C_2H_5$ (derived from L-alanine ethyl ester) | 150 | 0.3 | Fair | 10 |
| 23 | S—alpha-methyl benzyl | 177 | 0.01 | Poor | 28.5 |

[1] The chiral group of the 4-nitroaryl urea compound is represented by $R^3$ of formula II. In Examples 18 through 21, inclusive, the aryl group was $4\text{-}NO_2C_6H_4\text{-}$. In Example 22, the aryl group was $2\text{-}CH_3O\text{-}4\text{-}NO_2C_6H_3\text{-}$. In Example 23, the aryl group was $4\text{-}NO_2\text{-}1\text{-}C_{10}H_6\text{-}$.
[2] d indicates that the compound melts with decomposition.
[3] The relative SHG efficiency is based on the SHG efficiency of urea, which has been assigned a value of 1.0.
[4] Powder quality refers to the clarity, lack of polycrystallinity, and size distribution of the crystal fragments as judged by microscopic examination. As powder quality improves, the measured SHG efficiency improves. F represents "fairly". V represents "very".
[5] mW represents megawatts.

TABLE III

| Example | D | I | D | I | D | I | D | I | D | I | D | I | D | I | D | I |
|---|---|---|---|---|---|---|---|---|---|---|---|---|---|---|---|---|
| 1 | 22.53 | 100 | 11.31 | 3 | 7.53 | 6 | 6.24 | 5 | 5.65 | 7 | 4.73 | 12 | 4.26 | 14 | 3.82 | 4 |
|   | 3.76 | 9 | 3.70 | 10 | 3.55 | 10 | 3.301 | 8 | 3.254 | 8 | 3.219 | 4 | 3.041 | 10 | 2.789 | 3 |
| 1A | 6.89 | 71 | 5.97 | 16 | 5.16 | 59 | 4.20 | 38 | 4.13 | 9 | 3.64 | 100 | 3.43 | 40 | 3.35 | 7 |
|   | 3.211 | 13 | 2.852 | 40 | 2.721 | 12 | 2.542 | 5 | 2.423 | 11 | — | — | — | — | — | — |
| 2 | 12.32 | 90 | 12.12 | 100 | 6.12 | 54 | 6.06 | 90 | 5.64 | 17 | 5.46 | 31 | 4.43 | 20 | 4.07 | 14 |
|   | 4.03 | 24 | 3.80 | 24 | 3.75 | 35 | 3.72 | 14 | 3.403 | 14 | 3.376 | 17 | 3.351 | 13 | 3.027 | 14 |
| 2A | 12.15 | 83 | 6.07 | 100 | 5.63 | 41 | 5.43 | 64 | 4.42 | 45 | 4.37 | 52 | 4.23 | 28 | 4.04 | 25 |
|   | 3.76 | 77 | 3.69 | 32 | 3.52 | 31 | 3.364 | 78 | 3.306 | 37 | 3.016 | 53 | 2.764 | 23 | 2.700 | 18 |
| 3 | 8.76 | 35 | 6.85 | 16 | 5.85 | 88 | 5.66 | 100 | 5.23 | 27 | 4.36 | 30 | 4.30 | 30 | 4.22 | 37 |
|   | 4.04 | 15 | 4.00 | 18 | 3.67 | 26 | 3.60 | 42 | 3.493 | 24 | 3.299 | 31 | 2.927 | 20 | 2.824 | 17 |
| 4 | 12.51 | 7 | 8.65 | 58 | 6.26 | 18 | 5.55 | 10 | 5.42 | 100 | 4.34 | 32 | 4.17 | 9 | 3.94 | 45 |
|   | 3.82 | 4 | 3.315 | 7 | 3.030 | 18 | 2.924 | 12 | 2.891 | 30 | 2.823 | 5 | 2.778 | 9 | 2.712 | 8 |
| 5 | 13.08 | 57 | 6.51 | 33 | 5.50 | 5 | 5.25 | 1 | 4.51 | 1 | 4.32 | 100 | 4.24 | 4 | 3.59 | 10 |
|   | 3.386 | 3 | 3.240 | 15 | 2.910 | 3 | 2.764 | 8 | 2.729 | 1 | 2.587 | 16 | 2.422 | 4 | 2.318 | 8 |
| 6 | 10.71 | 13 | 7.00 | 22 | 6.55 | 8 | 5.72 | 40 | 5.35 | 9 | 4.86 | 100 | 4.77 | 17 | 4.36 | 44 |
|   | 3.90 | 18 | 3.85 | 8 | 3.56 | 12 | 3.126 | 10 | 2.906 | 9 | 2.855 | 9 | 2.773 | 10 | 2.697 | 8 |
| 7 | 13.21 | 31 | 6.62 | 33 | 5.80 | 95 | 5.43 | 46 | 4.93 | 64 | 4.42 | 88 | 3.74 | 38 | 3.66 | 26 |
|   | 3.55 | 28 | 3.438 | 100 | 3.313 | 19 | 2.955 | 37 | 2.902 | 45 | 2.819 | 26 | 2.711 | 22 | 2.647 | 19 |
| 8 | 7.04 | 41 | 5.60 | 18 | 5.04 | 26 | 4.72 | 62 | 4.66 | 42 | 4.59 | 100 | 4.47 | 46 | 4.42 | 59 |
|   | 4.38 | 42 | 4.27 | 20 | 4.12 | 35 | 4.06 | 20 | 4.01 | 19 | 3.96 | 34 | 3.86 | 22 | 3.324 | 18 |
| 8A | 16.60 | 34 | 5.84 | 30 | 5.53 | 7 | 5.26 | 15 | 5.10 | 100 | 4.55 | 37 | 4.45 | 36 | 4.32 | 25 |
|   | 4.14 | 15 | 3.95 | 15 | 3.90 | 26 | 3.77 | 19 | 3.62 | 40 | 3.443 | 50 | 3.115 | 10 | 2.771 | 10 |

[1] X-ray powder pattern

TABLE III-continued

| Example | \multicolumn{14}{c}{X-ray powder pattern[1]} |
|---|---|---|---|---|---|---|---|---|---|---|---|---|---|---|
| | D | I | D | I | D | I | D | I | D | I | D | I | D | I |
| 9 | 10.80 | 27 | 6.98 | 9 | 6.46 | 5 | 5.80 | 18 | 5.41 | 30 | 4.90 | 100 | 4.74 | 7 | 4.38 | 44 |
| | 3.91 | 8 | 3.86 | 3 | 3.61 | 6 | 3.52 | 7 | 3.149 | 7 | 2.922 | 9 | 2.839 | 5 | 2.706 | 6 |
| 10 | 8.71 | 81 | 6.31 | 68 | 5.25 | 54 | 4.72 | 36 | 4.60 | 14 | 4.38 | 65 | 4.19 | 44 | 3.97 | 100 |
| | 3.71 | 57 | 3.63 | 25 | 3.51 | 38 | 3.259 | 40 | 3.160 | 23 | 3.038 | 18 | 2.922 | 12 | 2.648 | 14 |
| 11 | 12.47 | 13 | 9.04 | 12 | 7.06 | 6 | 6.21 | 92 | 5.71 | 7 | 5.31 | 100 | 4.53 | 24 | 4.36 | 5 |
| | 4.14 | 11 | 3.88 | 7 | 3.71 | 9 | 3.52 | 5 | 3.243 | 4 | 3.183 | 4 | 3.014 | 5 | 2.982 | 4 |
| 12 | 8.78 | 14 | 7.66 | 13 | 6.22 | 58 | 5.38 | 38 | 5.06 | 100 | 4.60 | 81 | 4.39 | 38 | 4.19 | 10 |
| | 3.70 | 22 | 3.60 | 9 | 3.486 | 18 | 3.061 | 9 | 2.931 | 22 | 2.684 | 7 | 2.551 | 11 | 2.327 | 6 |
| 13 | 10.61 | 9 | 9.12 | 17 | 8.59 | 11 | 6.64 | 7 | 4.59 | 19 | 4.52 | 18 | 4.14 | 14 | 3.92 | 33 |
| | 3.88 | 17 | 3.83 | 14 | 3.440 | 19 | 3.317 | 100 | 3.290 | 13 | 3.233 | 9 | 3.841 | 8 | 2.769 | 8 |
| 14 | 6.93 | 94 | 6.19 | 56 | 5.35 | 100 | 5.27 | 62 | 4.76 | 82 | 4.57 | 78 | 4.14 | 58 | 4.05 | 46 |
| | 4.02 | 42 | 3.96 | 64 | 3.76 | 33 | 3.69 | 34 | 3.63 | 47 | 3.55 | 39 | 3.51 | 54 | 3.467 | 66 |
| 15 | 9.08 | 95 | 6.78 | 63 | 6.30 | 31 | 5.71 | 21 | 5.35 | 100 | 5.18 | 24 | 4.61 | 65 | 4.54 | 35 |
| | 4.20 | 20 | 3.82 | 50 | 3.68 | 35 | 3.485 | 32 | 3.386 | 48 | 3.183 | 33 | 2.998 | 40 | 2.775 | 30 |
| 16 | 10.58 | 75 | 6.94 | 17 | 5.84 | 18 | 5.69 | 84 | 4.83 | 74 | 4.74 | 32 | 4.33 | 100 | 4.08 | 21 |
| | 3.88 | 54 | 3.84 | 45 | 3.59 | 15 | 3.55 | 13 | 3.345 | 14 | 3.168 | 18 | 3.120 | 16 | 2.687 | 18 |
| 17 | 9.06 | 19 | 7.03 | 4 | 5.23 | 67 | 5.18 | 100 | 5.04 | 25 | 5.00 | 27 | 4.36 | 6 | 4.04 | 5 |
| | 3.96 | 7 | 3.418 | 4 | 3.305 | 6 | 3.259 | 6 | 3.053 | 6 | 2.605 | 7 | 2.575 | 5 | 2.512 | 3 |
| 18 | 18.19 | 23 | 9.01 | 15 | 6.12 | 17 | 4.78 | 39 | 4.57 | 68 | 4.38 | 61 | 4.07 | 16 | 3.92 | 14 |
| | 3.73 | 100 | 3.67 | 70 | 3.441 | 34 | 3.274 | 46 | 3.228 | 39 | 3.113 | 70 | 2.947 | 13 | 2.699 | 14 |
| 19 | 7.08 | 9 | 6.11 | 14 | 5.67 | 9 | 5.34 | 83 | 4.62 | 16 | 3.61 | 44 | 3.50 | 57 | 3.43 | 45 |
| | 3.429 | 44 | 3.327 | 100 | 3.287 | 67 | 3.203 | 29 | 3.077 | 15 | 2.920 | 16 | 2.762 | 21 | 2.647 | 9 |
| 20 | 17.55 | 70 | 8.89 | 50 | 6.56 | 53 | 5.83 | 94 | 5.50 | 100 | 5.35 | 22 | 4.46 | 30 | 4.02 | 39 |
| | 3.93 | 36 | 3.81 | 99 | 3.68 | 51 | 3.232 | 71 | 3.139 | 64 | 3.037 | 33 | 2.982 | 19 | 2.922 | 43 |
| 21 | 6.28 | 12 | 5.99 | 27 | 5.59 | 21 | 5.46 | 35 | 5.32 | 41 | 4.46 | 13 | 4.38 | 42 | 4.34 | 75 |
| | 3.55 | 42 | 3.51 | 49 | 3.260 | 100 | 3.141 | 25 | 3.102 | 14 | 2.775 | 14 | 2.748 | 11 | 2.717 | 12 |
| 22 | 11.50 | 31 | 7.44 | 64 | 6.74 | 17 | 6.01 | 15 | 4.57 | 75 | 4.21 | 14 | 4.15 | 14 | 3.78 | 100 |
| | 3.73 | 39 | 3.63 | 17 | 3.469 | 19 | 3.427 | 13 | 3.354 | 20 | 3.293 | 42 | 2.892 | 17 | 2.844 | 15 |
| 23 | 9.33 | 14 | 7.10 | 26 | 6.36 | 100 | 4.66 | 16 | 4.30 | 19 | 4.07 | 27 | 3.80 | 74 | 3.64 | 82 |
| | 3.51 | 13 | 3.414 | 33 | 3.320 | 95 | 3.257 | 50 | 3.201 | 25 | 3.169 | 20 | 3.113 | 13 | 2.862 | 12 |

[1]D represents the lattice spacing in Angstrom units.
I represents intensity in percentages relative to the strongest signal.

TABLE IV

| Example | Solvent of crystallization |
|---|---|
| 1 | Tetrahydrofuran/heptane |
| 1A | n-Propanol |
| 2 | Methyl t-butyl ether/cyclohexane (1/10) |
| 2A | Crystallized from reaction in chlorobenzene |
| 3 | Chlorobenzene |
| 4 | Chlorobenzene |
| 5 | Chlorobenzene |
| 6 | Crystallized from reaction in chlorobenzene |
| 7 | Aqueous methanol |
| 8 | Selective partial evaporation of ethanol/water (2/1) |
| 8A | Toluene/heptane |
| 9 | Crystallized from reaction in chlorobenzene |
| 10 | Precipitated from reaction in chlorobenzene |
| 11 | Precipitated from reaction in chlorobenzene |
| 12 | Cold chlorobenzene |
| 13 | Crystallized from reaction in toluene |
| 14 | Ethanol/water (7/9) |
| 15 | Ethanol/water (1/1) |
| 16 | Ethanol/water (2/3) |
| 17 | Nitrobenzene |
| 18 | Evaporation of acetone solution |
| 19 | Crystallized from reaction in toluene |
| 20 | Crystallized from reaction in toluene |
| 21 | Crystallized from reaction in toluene |
| 22 | Evaporation of ethanol solution |
| 23 | Crystallized from reaction in chlorobenzene |

EXAMPLE 24

4-Nitrophenyl isocyanate was freshly purified by filtration of a toluene solution followed by boiling off most of the toluene and evaporating of the remainder upon crystallization. It had a melting point of 55°–57° C. The 4-nitrophenyl isocyanate (1.674 g, 0.01 mole) was dissolved in ca. 15 ml toluene. To this solution was added 1.30 g (0.011 mole) ethyl L-lactate and 1 drop dry pyridine. A slight precipitate formed. After 24 hours, the solvent was filtered off, and the filtrate was allowed to evaporate to an oil, which, on standing, crystallized after one week. Because excess ethyl lactate had been used, the product was washed with three 40 ml portions of water and allowed to dry overnight. The crystalline residue, 2.49 g (88% yield), had a melting point of 93°–95° C. and was extremely pale yellow. The SHG efficiency was very high, about 40 times that of the standard urea sample.

The procedure of Example 24 was further utilized to prepare the urethanes set forth and described in Tables V, VI, VII, VIII, IX, XI, XII, and XIII. Table V sets forth relative SHG efficiency of 4-nitrophenyl urethane compounds that differ in the chiral group. Table VI sets forth the X-ray powder pattern for the urethane compounds of Table V. Table VII sets forth the crystallization solvents for the urethane compounds of Table V. Table VIII sets forth relative SHG efficiency of urethane compounds that differ in the aryl substitutent. Table IX sets forth the X-ray powder pattern for the urethane compounds of Table VIII. Table X sets forth the crystallization solvents for the urethane compounds of Table VIII. Table XI sets forth relative SHG efficiency of 3-nitrophenyl urethane compounds that differ in the chiral group. Table XII sets forth the X-ray powder pattern for the urethane compounds of Table XI. Table XIII sets forth the crystallization solvents for the urethane compounds of Table XI.

TABLE V

| Example | Chiral group of 4-nitrophenyl urethane compound[1] | m.p. (°C.) | Relative SHG efficiency[2] | Powder quality[3] | Power (mW)[4] |
|---|---|---|---|---|---|
| 24 | $CH_3$<br>\|<br>—CHCO$_2$C$_2$H$_5$(S)<br>*<br>(From S(—) ethyl lactate) | 95–97 | 30 | Good | 10 |
| 25 | —Nopyl<br>(From 1-nopol) | 76 | 0.001 | Fair | 12 |
| 26 | $CH_3$<br>\|<br>—CH$_2$CHCO$_2$CH$_3$(R)<br>* | 103 | 0.1 | F. Good | 13 |
| 27 | $CH_3$<br>\|<br>—CHCO$_2$CH$_3$(S)<br>*<br>(From S(—) methyl lactate) | 123 | 30 | F. Good | 12 |
| 28 | *<br>—CH$_2$CHCH$_2$CH$_3$<br>\|<br>$CH_3$<br>(From D(—)-2-methyl-butanol) | 52 | 20 | Poor | 12 |
| 29 | —Menthyl<br>(From 1-menthol) | 116 | 0.03 | Good | 10 |
| 30 | $CH_3$<br>\|<br>—CH$_2$CHCO$_2$C$_4$H$_9$—n<br>*        (R) | 51 | 0.01 | Good | 11 |
| 31 | $CH_3$<br>\|<br>—CHCH$_2$CH$_3$(S)<br>* | 57 | 0.007 | Good | 8 |
| 32 | $CH_3$<br>\|<br>—CH(CH$_2$)$_5$CH$_3$<br>*<br>(from 1-2-octanol) | 116 | 0.02 | Fair | 10 |
| 33 | $CH_3$<br>\|<br>—CH—CO$_2$C$_4$H$_9$—n(S)<br>*<br>(from S butyl lactate) | 48 | 6 | Fair | 11 |
| 34 | —CH$_2$—CH(O—C(CH$_3$)$_2$—O—CH$_2$) (S) | 113 | 3.5 | Fair | 10 |
| 35 | *<br>—CH$_2$—CH—CH$_2$OH(S)<br>\|<br>OH | 173 | 0.008 |  | 10 |

[1]The chiral group is represented by R$^3$ of formula II. The asymmetric carbon atom is represented by C*.
[2]The relative SHG efficiency is based on the SHG efficiency of urea, which has been assigned a value of 1.0.
[3]Powder quality refers to the clarity, lack of polycrystallinity, and size distribution of the crystal fragments as judged by microscopic examination. As powder quality improves, the measured SHG efficiency improves. F represents "fairly". V represents "very".
[4]mW represents megawatts.

TABLE VI

| Example | \multicolumn{16}{c}{X-ray powder pattern[1]} |
|---|---|---|---|---|---|---|---|---|---|---|---|---|---|---|---|---|
|  | D | I | D | I | D | I | D | I | D | I | D | I | D | I | D | I |
| 24 | 9.82 | 47 | 5.71 | 42 | 5.58 | 77 | 5.45 | 47 | 4.88 | 70 | 4.77 | 27 | 4.24 | 98 | 4.03 | 100 |
|  | 3.80 | 80 | 3.70 | 26 | 3.66 | 55 | 3.473 | 40 | 3.295 | 83 | 3.169 | 44 | 3.133 | 61 | 3.056 | 20 |
| 25 | 21.61 | 100 | 6.47 | 11 | 5.88 | 23 | 5.48 | 57 | 5.03 | 52 | 4.91 | 28 | 4.78 | 42 | 4.56 | 42 |
|  | 4.34 | 50 | 4.13 | 31 | 3.99 | 20 | 3.69 | 21 | 3.372 | 16 | 3.319 | 23 | 3.206 | 20 | 3.043 | 31 |
| 26 | 11.14 | 11 | 6.51 | 18 | 6.38 | 10 | 5.66 | 23 | 5.06 | 11 | 4.90 | 24 | 4.51 | 20 | 4.40 | 40 |
|  | 4.35 | 78 | 4.20 | 48 | 4.00 | 45 | 3.92 | 28 | 3.90 | 28 | 3.65 | 99 | 3.340 | 27 | 3.293 | 100 |
| 27 | 11.45 | 9 | 7.37 | 4 | 6.81 | 14 | 5.68 | 4 | 4.68 | 13 | 4.50 | 100 | 4.31 | 4 | 4.18 | 7 |
|  | 3.84 | 24 | 3.65 | 9 | 3.56 | 7 | 3.232 | 31 | 2.957 | 7 | 2.661 | 4 | 2.496 | 5 | 2.343 | 4 |

TABLE VI-continued

| Example | \multicolumn{14}{c}{X-ray powder pattern[1]} | | | | | | | | | | | | | |
|---|---|---|---|---|---|---|---|---|---|---|---|---|---|---|
| | D | I | D | I | D | I | D | I | D | I | D | I | D | I |
| 27A | 11.57 | 39 | 6.85 | 19 | 5.78 | 7 | 5.07 | 7 | 4.71 | 22 | 4.51 | 100 | 4.20 | 7 | 3.85 | 28 |
| | 3.66 | 20 | 3.57 | 14 | 3.237 | 43 | 2.969 | 7 | 2.906 | 8 | 2.346 | 10 | 2.319 | 14 | 2.301 | 9 |
| 28 | 20.21 | 100 | 10.15 | 12 | 5.76 | 6 | 5.10 | 60 | 4.70 | 6 | 4.17 | 9 | 4.03 | 6 | 3.78 | 9 |
| | 3.65 | 10 | 3.50 | 36 | 3.438 | 19 | 3.377 | 15 | 3.218 | 21 | 3.052 | 6 | 2.907 | 7 | 2.539 | 6 |
| 29 | 17.63 | 100 | 8.62 | 70 | 8.14 | 10 | 5.88 | 16 | 5.16 | 34 | 4.84 | 20 | 4.66 | 10 | 4.56 | 12 |
| | 4.18 | 13 | 4.10 | 25 | 3.82 | 10 | 3.373 | 20 | 3.346 | 40 | 3.106 | 12 | 2.929 | 13 | 2.854 | 22 |
| 30 | 14.92 | 100 | 7.43 | 10 | 5.61 | 6 | 5.30 | 22 | 4.93 | 60 | 4.50 | 15 | 4.19 | 37 | 4.10 | 7 |
| | 3.86 | 52 | 3.70 | 20 | 3.63 | 37 | 3.55 | 46 | 3.434 | 27 | 3.355 | 12 | 3.281 | 15 | 3.147 | 6 |
| 31 | 8.33 | 10 | 7.03 | 13 | 6.12 | 66 | 5.08 | 22 | 4.80 | 6 | 4.67 | 35 | 4.17 | 17 | 3.94 | 100 |
| | 3.81 | 25 | 3.76 | 7 | 3.62 | 14 | 3.57 | 15 | 3.443 | 31 | 3.378 | 19 | 3.148 | 8 | 2.680 | 20 |
| 32 | 11.32 | 42 | 6.51 | 3 | 6.26 | 5 | 4.65 | 33 | 4.45 | 6 | 4.11 | 100 | 3.96 | 36 | 3.78 | 36 |
| | 3.60 | 3 | 3.54 | 3 | 3.497 | 4 | 3.228 | 12 | 3.196 | 10 | 3.129 | 9 | 2.929 | 6 | 2.662 | 3 |
| 33 | 14.30 | 77 | 5.91 | 35 | 5.68 | 19 | 5.25 | 18 | 4.83 | 19 | 4.57 | 100 | 4.36 | 44 | 4.24 | 30 |
| | 4.11 | 27 | 4.05 | 15 | 3.90 | 34 | 3.57 | 24 | 3.383 | 26 | 3.320 | 17 | 3.141 | 24 | 3.076 | 21 |
| 34 | 12.61 | 55 | 6.35 | 18 | 6.06 | 14 | 5.35 | 20 | 4.84 | 15 | 4.76 | 23 | 4.70 | 11 | 4.44 | 15 |
| | 4.23 | 26 | 4.15 | 100 | 3.90 | 42 | 3.83 | 35 | 3.64 | 17 | 3.180 | 80 | 3.148 | 69 | 3.110 | 30 |
| 35 | 4.58 | 12 | 4.34 | 100 | 4.28 | 30 | 4.18 | 17 | 3.87 | 19 | 3.81 | 87 | 3.76 | 14 | 3.57 | 17 |
| | 3.372 | 28 | 3.386 | 41 | 3.244 | 16 | 3.185 | 45 | 3.037 | 17 | 2.378 | 10 | 2.295 | 37 | 1.930 | 11 |

[1]D represents the lattice spacing in Angstrom units.
I represents intensity in percentages relative to the strongest signal.

TABLE VII

| Example | Solvent of crystallization |
|---|---|
| 24 | Evaporation of ethanol solution |
| 25 | Evaporation of solution in CH$_2$Cl$_2$/isooctane, then washed with CF$_2$ClCFCl$_2$ |
| 26 | Toluene |
| 27 | Partial (selective) evaporation of methyl t-butyl ether/isooctane solution |
| 28 | Cold CF$_2$ClCFCl$_2$ |
| 29 | Neat, then washed with CF$_2$ClCFCl$_2$ |
| 30 | Neat, then washed with CF$_2$ClCFCl$_2$ |
| 31 | Neat, then washed with CF$_2$ClCFCl$_2$ |
| 32 | Cold CF$_2$ClCFCl$_2$/C$_7$F$_{16}$ (4/1) |
| 33 | Partial (selective) evaporation of methyl t-butyl ether/isooctane solution |
| 34 | Ethanol |
| 35 | Methanol/acetic acid (4/1) |

TABLE VIII

| Example | Aryl group in chiral urethane[1] | m.p. (°C.) | Relative SHG efficiency[2] | Powder quality[3] | Power (mW)[4] |
|---|---|---|---|---|---|
| 36 | 2-Cl—4-NO$_2$—C$_6$H$_3$— | 53 | 0.5 | Fair | 10 |
| 37 | 2-CH$_3$—4-NO$_2$—C$_6$H$_3$— | 71 | 0.001 | Poor | 10 |
| 38 | 4-N≡C—C$_6$H$_4$— | 53 | 0.2 | Poor | 10 |

[1]The chiral group is —C*HCO$_2$C$_2$H$_5$.
         |
        CH$_3$
[2]The relative SHG efficiency is based on the SHG efficiency of urea, which has been assigned a value of 1.0.
[3]Powder quality refers to the clarity, lack of polycrystallinity, and size distribution of the crystal fragments as judged by microscopic examination. As powder quality improves, the measured SHG efficiency improves. F represents "fairly". V represents "very".
[4]mW represents megawatts.

TABLE IX

| Example | \multicolumn{14}{c}{X-ray powder pattern[1]} | | | | | | | | | | | | | |
|---|---|---|---|---|---|---|---|---|---|---|---|---|---|---|
| | D | I | D | I | D | I | D | I | D | I | D | I | D | I |
| 36 | 14.62 | 100 | 7.38 | 24 | 5.24 | 7 | 5.18 | 8 | 4.23 | 12 | 3.98 | 26 | 3.93 | 14 | 3.84 | 10 |
| | 3.76 | 13 | 3.61 | 17 | 3.56 | 8 | 3.501 | 7 | 3.378 | 14 | 3.319 | 11 | 3.223 | 11 | 3.188 | 12 |
| 37 | 14.20 | 45 | 7.35 | 100 | 7.25 | 81 | 7.13 | 56 | 5.99 | 39 | 4.76 | 48 | 4.62 | 45 | 4.51 | 31 |
| | 4.39 | 31 | 4.05 | 50 | 3.78 | 38 | 3.400 | 100 | 3.348 | 31 | 3.291 | 45 | 3.257 | 43 | 3.081 | 40 |
| 38 | 11.36 | 16 | 9.81 | 22 | 5.95 | 22 | 5.82 | 25 | 5.66 | 18 | 5.26 | 17 | 4.89 | 100 | 4.64 | 18 |
| | 4.47 | 69 | 4.30 | 40 | 3.97 | 25 | 3.85 | 24 | 3.71 | 55 | 3.56 | 66 | 3.267 | 27 | 2.715 | 15 |

[1]D represents the lattice spacing in Angstrom units.
I represents intensity in percentages relative to the strongest signal.

TABLE X

| Example | Solvent of crystallization |
|---|---|
| 36 | Cold CF$_2$ClCFCl$_2$ |
| 37 | Cold CF$_2$ClCFCl$_2$ |
| 38 | Neat (Very slow) |

TABLE XI

| Example | Chiral group of 3-nitrophenyl urethane compound[1] | m.p. (°C.) | Relative SHG efficiency[2] | Powder quality[3] | Power (mW)[4] |
|---|---|---|---|---|---|
| 39 | CH$_3$<br>   \|<br>—CH$_2$C*HCH$_2$CH$_3$<br>(D(—)-2-methyl-butanol) | 65 | 0.04<br>0.01 | Good<br>Fair | 12<br>13 |
| 40 | CH$_3$<br>   \|<br>—C*H(CH$_2$)$_5$CH$_3$<br>(l-2-octanol) | 44 | 0.5 | Poor | 10 |
| 41 | menthyl<br>(l-menthol) | 83 | 0.03 | Fair | 13 |

[1]The chiral group is represented by R$^3$ of formula III. The asymmetric carbon atom is represented by C*.
[2]The relative SHG efficiency is based on the SHG efficiency of urea, which has been assigned a value of 1.0.
[3]Powder quality refers to the clarity, lack of polycrystallinity, and size distribution of the crystal fragments as judged by microscopic examination. As powder quality improves, the measured SHG efficiency improves. F represents "fairly". V represents "very".
[4]mW represents megawatts.

TABLE XII

| Example | \multicolumn{14}{c}{X-ray powder pattern[1]} |
|---|---|---|---|---|---|---|---|---|---|---|---|---|---|---|
|  | D | I | D | I | D | I | D | I | D | I | D | I | D | I | D | I |
| 39 | 11.47 | 33 | 11.27 | 37 | 5.42 | 65 | 5.37 | 42 | 4.63 | 25 | 4.53 | 23 | 4.29 | 33 | 3.89 | 30 |
|  | 3.84 | 100 | 3.73 | 35 | 3.66 | 28 | 3.62 | 31 | 3.58 | 40 | 3.56 | 66 | 3.54 | 66 | 2.922 | 18 |
| 40 | 15.10 | 80 | 5.56 | 40 | 5.45 | 35 | 5.22 | 37 | 4.99 | 20 | 4.86 | 100 | 4.47 | 35 | 4.10 | 70 |
|  | 3.79 | 80 | 3.72 | 40 | 3.63 | 65 | 3.50 | 65 | 3.394 | 35 | 3.349 | 20 | 3.217 | 25 | 3.169 | 35 |
| 41 | 20.34 | 30 | 17.75 | 28 | 14.33 | 50 | 8.52 | 40 | 8.00 | 43 | 5.83 | 44 | 5.79 | 37 | 4.74 | 100 |
|  | 4.68 | 72 | 4.61 | 58 | 4.52 | 90 | 4.30 | 36 | 4.25 | 36 | 4.23 | 30 | 4.06 | 39 | 3.85 | 37 |

[1] D represents lattice spacing in Angstrom units.
I represents intensity in percentage relative to the strongest signal.

TABLE XIII

| Example | Solvent of crystallization |
|---|---|
| 39 | Evaporation of solution in $CF_2ClCFCl_2$/isooctane/methyl t-butyl ether |
| 40 | Evaporation of solution in $CH_2Cl_2$/methyl tertbutyl ether |
| 41 | Evaporation of solution in cyclohexane, washing with $CF_2ClCFCl_2$ |

Compounds of this invention may employ chiral alpha-amino acid moieties or alpha-amino acid ester moieties, as shown in Examples 19, 21 and 22. However, these materials are regarded as least desirable because, unlike the other ureas, they are capable of ready racemization. It is well known that chiral amino acids and especially their N-acyl derivatives undergo racemization at higher tempeatures or in the presence of weak acids and bases. See, for example, P. A. Levene, J. Biol. Chem. 76 299 (1928); M. Bergmann and L. Zervas, Biochem. Zeitschrift 203 280 (1928); V. DuVigneaud, J. Biol. Chem. 96 511 (1932) and 98 295 (1932); and I. Sakieki, Nippon Kagaku Zasshi, 80 1035 (1959).

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A second harmonic generator comprising a laser source of coherent light radiation at a fixed fundamental frequency, an organic molecular crystalline compound, means for directing the output radiation of the laser onto the compound, and output means for utilizing the second harmonic frequency, said compound being a chiral N-aryl carbamyl compound in which the nitrogen of the carbamyl group is directly bonded to the aryl group and which crystallizes in a non-centrosymmetric configuration, said compound being transparent to radiation at said fixed fundamental frequency and said second harmonic frequency.

2. A second harmonic generator comprising a laser source of coherent light radiation at a fixed fundamental frequency, an organic molecular crystalline compound, means for directing the output radiation of the laser onto the compound, and output means for utilizing the second harmonic frequency, said compound being a chiral N-aryl carbamyl compound which crystallizes in a non-centrosymmetric configuration, said compound being transparent to radiation at said fixed fundamental frequency and said second harmonic frequency, wherein said organic crystalline compound is represented by the formula:

where
$R^1$ represents an aryl group having from six to eighteen carbon atoms,
$R^2$ represents hydrogen or alkyl group having one to six carbon atoms,
$R^3$ represents a carbon-containing chiral group, and
$R^4$ represents hydrogen, alkyl group having one to six carbon atoms, a chiral group, or $R^3$ and $R^4$ together, along with the nitrogen atom to which they are attached, form a catenated heterocyclic ring containing from 3 to 7 ring members.

3. The second harmonic generator of claim 2 wherein the chiral group $R^3$ has an asymmetric carbon atom which is attached to the urea nitrogen atom or to a carbon atom bonded to the urea nitrogen atom.

4. The second harmonic generator of claim 2 wherein the chiral group $R^3$ has an asymmetric carbon atom which is attached to the urethane oxygen atom or to a carbon atom bonded to the urethane oxygen atom.

5. The second harmonic generator of claim 2 wherein the chiral group $R^3$ has an asymmetric carbon atom attached to the urea nitrogen atom.

6. The second harmonic generator of claim 2 wherein the chiral group $R^3$ has an asymmetric carbon atom attached to the urethane oxygen atom.

7. The second harmonic generator of claim 1 wherein the laser is a Nd-YAG laser.

8. The second harmonic generator of claim 1 wherein said laser is a solid-state laser.

9. A process for converting a fixed fundamental frequency of coherent laser light into a second harmonic frequency which comprises passing said laser light through a nonlinear optical element comprising an organic molecular crystalline compound, said compound being a chiral N-aryl carbamyl compound in which the nitrogen of the carbamyl group is directly bonded to the aryl group and which crystallizes in a non-centrosymmetric configuration, said compound being transparent to said fixed fundamental frequency and to said second harmonic frequency.

10. A process for converting a fixed fundamental frequency of coherent laser light into a second harmonic frequency which comprises passing said laser light through a nonlinear optical element comprising an organic molecular crystalline compound, said compound being a chiral N-aryl carbamyl compound which crystallizes in a noncentrosymmetric configuration, said compound being transparent to said fixed fundamental frequency and to said second harmonic frequency, wherein said organic molecular crystalline compound is represented by the formula:

where
- $R^1$ represents an aryl group having from six to eighteen carbon atoms,
- $R^2$ represents hydrogen or alkyl group having one to six carbon atoms,
- $R^3$ represents a carbon-containing chiral group, and
- $R^4$ represents hydrogen, alkyl group having one to six carbon atoms, a chiral group, or $R^3$ and $R^4$ together, along with the nitrogen atom to which they are attached, form a catenated heterocyclic ring containing from 3 to 7 ring members.

11. The process of claim 10 wherein the chiral group $R^3$ has an asymmetric carbon atom which is attached to the urea nitrogen atom or to a carbon atom bonded to the urea nitrogen atom.

12. The process of claim 10 wherein the chiral group $R^3$ has an asymmetric carbon atom which is attached to the urethane oxygen atom or to a carbon atom bonded to the urethane oxygen atom.

13. The process of claim 10 wherein the chiral group $R^3$ has an asymmetric carbon atom attached to the urea nitrogen atom.

14. The process of claim 10 wherein the chiral group $R^3$ has an asymmetric carbon atom attached to the urethane oxygen atom.

* * * * *

UNITED STATES PATENT AND TRADEMARK OFFICE
CERTIFICATE OF CORRECTION

PATENT NO. : 4,818,899

DATED : April 4, 1989

INVENTOR(S) : George V.D. Tiers

It is certified that error appears in the above-identified patent and that said Letters Patent is hereby corrected as shown below:

In Column 9, Line 30, please delete the phrase "(derived from L-2 amino-1-propanol; L-alaninol) and insert therefor --(derived from L-2-amino propanol-1; L-alaninol)--.

Signed and Sealed this

Eleventh Day of September, 1990

Attest:

HARRY F. MANBECK, JR.

Attesting Officer

Commissioner of Patents and Trademarks